(12) United States Patent
Glaser-Seidnitzer et al.

(10) Patent No.: US 10,803,980 B2
(45) Date of Patent: Oct. 13, 2020

(54) METHOD, APPARATUS, AND COMPUTER PROGRAM PRODUCT FOR PREPARING A MEDICAL REPORT

(71) Applicants: Karlheinz Glaser-Seidnitzer, Fürth (DE); Andrew John Hewett, Erlangen (DE); Martin Huber, Uttenreuth (DE); Gerhard Kohl, Neunkirchen am Brand (DE); Michael Rusitska, Utternreuth (DE)

(72) Inventors: Karlheinz Glaser-Seidnitzer, Fürth (DE); Andrew John Hewett, Erlangen (DE); Martin Huber, Uttenreuth (DE); Gerhard Kohl, Neunkirchen am Brand (DE); Michael Rusitska, Utternreuth (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 1023 days.

(21) Appl. No.: 14/869,947

(22) Filed: Sep. 29, 2015

(65) Prior Publication Data
US 2016/0092656 A1 Mar. 31, 2016

(30) Foreign Application Priority Data
Sep. 30, 2014 (DE) .......................... 10 2014 219 841

(51) Int. Cl.
*G16H 15/00* (2018.01)

(52) U.S. Cl.
CPC .................................. *G16H 15/00* (2018.01)

(58) Field of Classification Search
CPC ........ G16H 15/00; G16H 10/60; G16H 30/00; G16H 30/20
See application file for complete search history.

(56) References Cited

U.S. PATENT DOCUMENTS

| | | | | |
|---|---|---|---|---|
| 2008/0184100 A1* | 7/2008 | Selig | ..................... | G06F 17/243 715/225 |
| 2010/0114597 A1* | 5/2010 | Shreiber | ............... | G06F 19/321 705/2 |

(Continued)

*Primary Examiner* — John P Go
(74) *Attorney, Agent, or Firm* — Lempia Summerfield Katz LLC (57) ABSTRACT

A user interacts with a medical imaging system and a medical reporting system to prepare a medical report. The medical reporting system includes report templates for medical reports. The report templates include placeholder fields with unique placeholder designations and metadata. After a user entry in the medical imaging system to select an image dataset, the image dataset and analysis tools are made available to the user. After a user entry in the medical reporting system to select a report template, a report template is made available. Placeholders contained in the selected report template are displayed with corresponding placeholder designations and metadata, automatically sent to the imaging system, and displayed as data requests. According to the data requests displayed, the data corresponding to the data requests is ascertained or determined by the user and assigned to the placeholder designations. A report editor automatically saves the data in the placeholder fields.

16 Claims, 6 Drawing Sheets

(56) References Cited

U.S. PATENT DOCUMENTS

| | | | |
|---|---|---|---|
| 2010/0131873 A1* | 5/2010 | Mejia | G16H 30/20 |
| | | | 715/764 |
| 2012/0253844 A1* | 10/2012 | Bocirnea | G16H 15/00 |
| | | | 705/3 |
| 2013/0251233 A1* | 9/2013 | Yang | G06T 7/0012 |
| | | | 382/132 |

* cited by examiner

METHOD, APPARATUS, AND COMPUTER PROGRAM PRODUCT FOR PREPARING A MEDICAL REPORT

This application claims the benefit of DE 10 2014 219 841.0, filed on Sep. 30, 2014, which is hereby incorporated by reference in its entirety.

BACKGROUND

The present embodiments relate to a method, apparatus, and computer program product for preparing a medical report.

Many medical questions may only be answered after an analysis of images of the inside of a patient. The images of a target area created in an examination are analyzed and assessed by the doctor. The results of the examination and the analysis are summarized in a medical report.

For a given clinical indication and a corresponding imaging study, the doctor is invited to set out a whole set of findings and analyses in a clinical report. Therefore, many doctors use predefined report forms or report templates for widespread and customary reports. In some cases, there are also regulations regarding the content of the various medical reports. These regulations may be specified both by the government and by health care institutions.

In many cases, imaging of the inside of the patient is today performed by radiologists using X-ray, computer tomography or magnetic resonance technology and summarized in imaging studies that may contain a plurality of individual images as well as volume images.

Typically, the results of the analyses (i.e., the medical report) are prepared by a special software application. Using the software application, by a report editor, the radiologist describes a whole series of individual results that may be organized according to a part of the body (e.g., head, neck, thorax, abdomen, pelvis, extremities) or a system (e.g., vascular system, bone).

Advances in imaging modalities, for example, with computer tomography or magnetic resonance imaging permit a growing number of quantitative analyses. The dimensions, the area, or the volume of a tumor may thus be determined quantitatively. Likewise, the extent of a vascular stenosis or the ejection fraction of the heart ventricle may today be measured in the image data.

Therefore, apart from a description of the findings, a radiological report also contains quantitative information. In addition, the report may contain key images as well as references to key images. However, this presupposes that the reporting system supports "rich content" or the recipient of the report has access to the imaging system.

In general, the imaging system is part of a picture archiving and communication system (PACS), while the reporting system is often part of a radiology information system (RIS). The doctor prepares the report in the RIS, while the doctor analyzes the images in the PACS.

With highly specialized image studies (e.g., with CT Calcium Scoring), the imaging system and the reporting system may be linked to each other to complete the report automatically using measurement values, key images, pictograms of the pathology, spreadsheet formats, analyses, etc. However, such linked systems are not to be used for anything other than particular clinical indication.

For many clinical indications (e.g., including an examination for non-specific complaints), such as, for example, "pains in the abdomen", there are no specialized image studies, and general 2D, 3D, or 3D+t displays are used for analysis of the imaging study. In these cases, the radiologist is to add the results and key images to the report manually. This approach is time-consuming and prone to error. For example, a measured value may be incorrectly recorded, and a key image may be wrongly identified during transcription.

There are also imaging applications that provide radiologists with limited support during preparation of the report. For example, these imaging applications permit results for the report to be highlighted, and these results are inserted in the report semi- or fully automatically. But even in this case, the radiologist is responsible for the images and results being correctly identified. If, for example, a measurement is to be provided for the value "diameter of descending aorta", and an additional measurement is to be provided for the value "diameter of aortic root", these are to be precisely identified by the radiologist to avoid erroneous interpretations.

For the preparation of a medical report from an imaging study, there are specialized applications for a few medical questions that are not to be used for other questions, however. For most clinical indications, there is only limited support for the doctor from corresponding applications for the preparation of a medical report. The measurement values and key images for the medical report are to be assigned by the doctor himself or herself and transcribed into the report. This approach is time-consuming as well as prone to error.

SUMMARY AND DESCRIPTION

The scope of the present invention is defined solely by the appended claims and is not affected to any degree by the statements within this summary.

The present embodiments may obviate one or more of the drawbacks or limitations in the related art. For example, options for preparing a medical report with which a plurality of different medical reports may be prepared in a simple and fail-safe manner are provided.

According to one or more of the present embodiments, a method for preparing a medical report is provided. A medical imaging system and a medical reporting system are provided. A user interacts with both the medical imaging system and the medical reporting system. The medical imaging system and the medical reporting system are linked to each other via a data line. The medical reporting system includes a collection of report templates for medical reports on various medical questions in electronic form. The report templates include placeholder fields with clear placeholder designations and metadata. The medical reporting system includes a report editor and includes the following procedural acts. After a user entry in the medical imaging system to select an image dataset for diagnosis, the medical imaging system provides the user with the image dataset for diagnosis and analysis tools for analysis of the image dataset for diagnosis. After a user entry in the medical reporting system to select a report template, the selected report template is made available by the reporting system. Placeholders contained in the selected report template with their placeholder designations and metadata are displayed and automatically sent to the imaging system as data requests. In accordance with the data requests displayed, the data corresponding to the data requests is ascertained or determined and assigned to the placeholder designations by the user using the analysis tools. The data ascertained or determined is automatically sent to the report editor by the imaging system together with the assigned placeholder designations. The report editor automatically stores the ascertained or determined data in the placeholder fields of the report form corresponding to the placeholder designations.

Instead of using indiscriminate blanks in the electronic report forms as hitherto, according to one or more of the present embodiments, placeholders with predetermined meanings and associated metadata are used. The user is prompted to complete the placeholders with corresponding findings, analyses, measurement values, and key images in the reporting system and/or in the imaging device. Each placeholder has a unique designation that is ideally taken from an ontology, such as, for example, RadLex. If a plurality of placeholders have the same designation (e.g., if a measured value is used once in the finding section and once in the impression section of a report), the placeholders are linked to each other using the same designation. The placeholders are displayed for the user in the sequence in which the placeholders are to be expediently processed. Because the electronic copy of the report used for the medical report thus describes data requests with unique placeholders, as soon as the user has ascertained or determined the data, the imaging system may send this requested data to the reporting system. Medical reports on various clinical indications may thereby be automatically completed with data from the imaging system.

The placeholders with their placeholder designations and metadata may be displayed by the reporting system. In an embodiment, the placeholders and metadata, alternatively or in addition to the display of the reporting system, are displayed by the imaging system. For example, display in addition to the reporting system is advantageous.

The user may thereby focus attention solely on the imaging system for analysis of the image data. The user no longer needs to alternate between the imaging system and the reporting system during the analysis.

An embodiment is characterized in that the respective placeholder designation is no longer displayed by the medical imaging system after the user has assigned ascertained or determined data to this placeholder designation. For this reason, only placeholders that are still to be processed by the user are still displayed. The risk of an erroneous assignment of analyses is thus further reduced.

A further embodiment is characterized in that data consecutively ascertained or determined by the user is automatically assigned consecutive placeholder designations by the medical imaging system. This feature further reduces susceptibility to errors when transcribing the measured values. This feature presupposes, however, that the user performs the analysis of image data in the same sequence in which the placeholders are arranged.

In one embodiment, the placeholder fields include explanatory data that is made available to the reporting system and/or the imaging system for display. The explanatory data may include a help text and/or graphic representations explaining the measurement. For example, the graphical representations may show where and/or how particular measured values are to be ascertained.

In another embodiment, the graphical data contains a model representation of the data requests. The model representation is fused in the image dataset for diagnosis. Consecutively ascertained or determined data is allocated to the model and automatically assigned to the placeholders. Susceptibility to errors during data transfer is further reduced thereby. This feature may be used advantageously for measurements that are used for the planning of an abdominal aortic aneurysm (AAA) stent placement.

DETAILED DESCRIPTION

Figure 1:
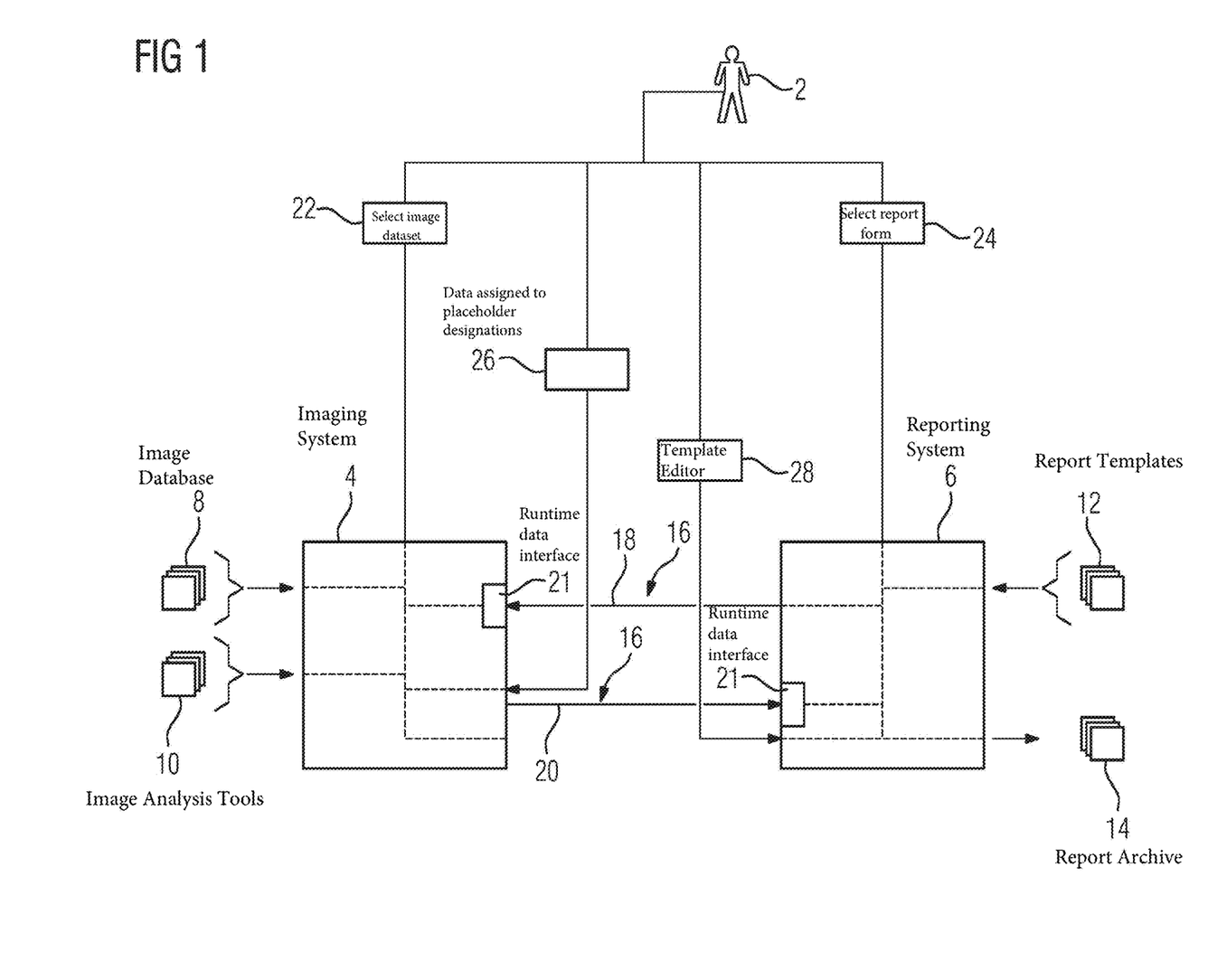
FIG. 1 shows examples of main components and procedural acts for preparing a medical report.

FIG. 1 shows a diagrammatic view of the main components and procedural steps for preparing a medical report. When preparing the medical report, a user 2 (e.g., a doctor) interacts both with an imaging system 4 and with a reporting system 6. The imaging system 4 is part of a comprehensive picture archiving and communication system (PACS) and provides a visual presentation and analysis of medical images. The imaging system 4 has access to an image database 8. Radiological images of patients are stored in the image database 8. In general, images of patients are created using various imaging modalities. These may include X-ray images, computer tomography (CT) images), magnetic resonance images, etc. The imaging system 4 includes a collection of different image analysis tools 10, with the aid of which the user 2 may quantitatively determine anatomical and functional details in the images shown.

In general, the reporting system 6 is part of a radiology information system (RIS) and includes a report editor 11. The report editor 11 has access to a collection of report templates 12 that include report templates tailored to various clinical indications. In addition, the report editor 11 has access to a report archive 14 in which the completed and released medical reports are stored.

The report forms in the collection of report templates 12 include placeholder fields with clear placeholder designations as well as associated metadata instead of the hitherto customary blanks. The configuration of the report forms is explained in more detail hereinafter with reference to FIG. 2 and FIG. 4.

The imaging system 4 and the reporting system 6 are linked to each other via a data line 16. The data line 16 includes a data request channel 18 and a data return channel 20, each of which connects to a runtime data interface 21.

When preparing a particular medical report for a particular patient, the user 2 first selects an appropriate image study or an appropriate image dataset of the patient from the image database 8 and uploads the image study or the image dataset to the imaging system 4 (see reference character 22 in FIG. 1). The user 2 selects an appropriate report form for answering the predetermined medical question (see reference character 24). The placeholders with metadata contained in the selected report template are transferred to the imaging system 4 via the data request channel 18.

The transferred placeholders with the associated metadata are displayed as a data request by the reporting system 6. In a user-friendly manner, the transferred placeholders with the associated metadata may be displayed by the imaging system 4 in an orderly sequence together with the selected image study. The order may be an expedient sequence of the analyses to be carried out in the image study.

According to the data requests displayed, the data corresponding to the data requests is ascertained or determined by the user 2 by the analysis tools 10 and assigned to the placeholder designations (see reference character 26). The allocated data may include measured values and/or key images. Key images are image displays in which characteristic details of the anatomy or of a function are shown. Further details of the procedural act 26 are described below with reference to FIG. 5 and FIG. 6.

After assignment of the requested data, such as measured values and/or key images, to the associated placeholder designations, this data is automatically sent to the reporting system 6 via the data return channel 20. The requested data is thereupon automatically transferred to the corresponding data fields by the unique placeholder designation. As soon as all the measured values and/or key images requested by the report form are present in the report form, the user 2 may complete and then release the report (see reference character 28). The report is then saved in the report archive 14.

If a new report form is selected by the user 2, any metadata still present is automatically updated in the imaging system 4.

While the method for preparing a medical report, including user interactions, is shown in FIG. 1, FIG. 2 shows a simplified component diagram of software and system parts of this method. The component diagram is displayed in the graphical modeling language unified modeling language (UML). FIG. 2 is divided into a total of three drawing pages with the subfigures FIG. 2A, FIG. 2B and FIG. 2C. As is customary in the modeling language UML, the designations in FIG. 2 are in English.

Figure 2:
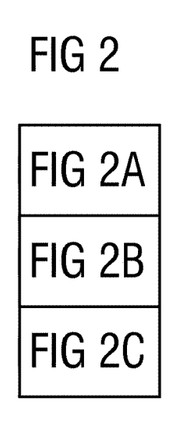
FIG. 2A to 2C show a simplified component diagram of software and system parts of one embodiment of a method for preparing a medical report, presented in the graphical modeling language unified modeling language (UML)
Figure 2A:
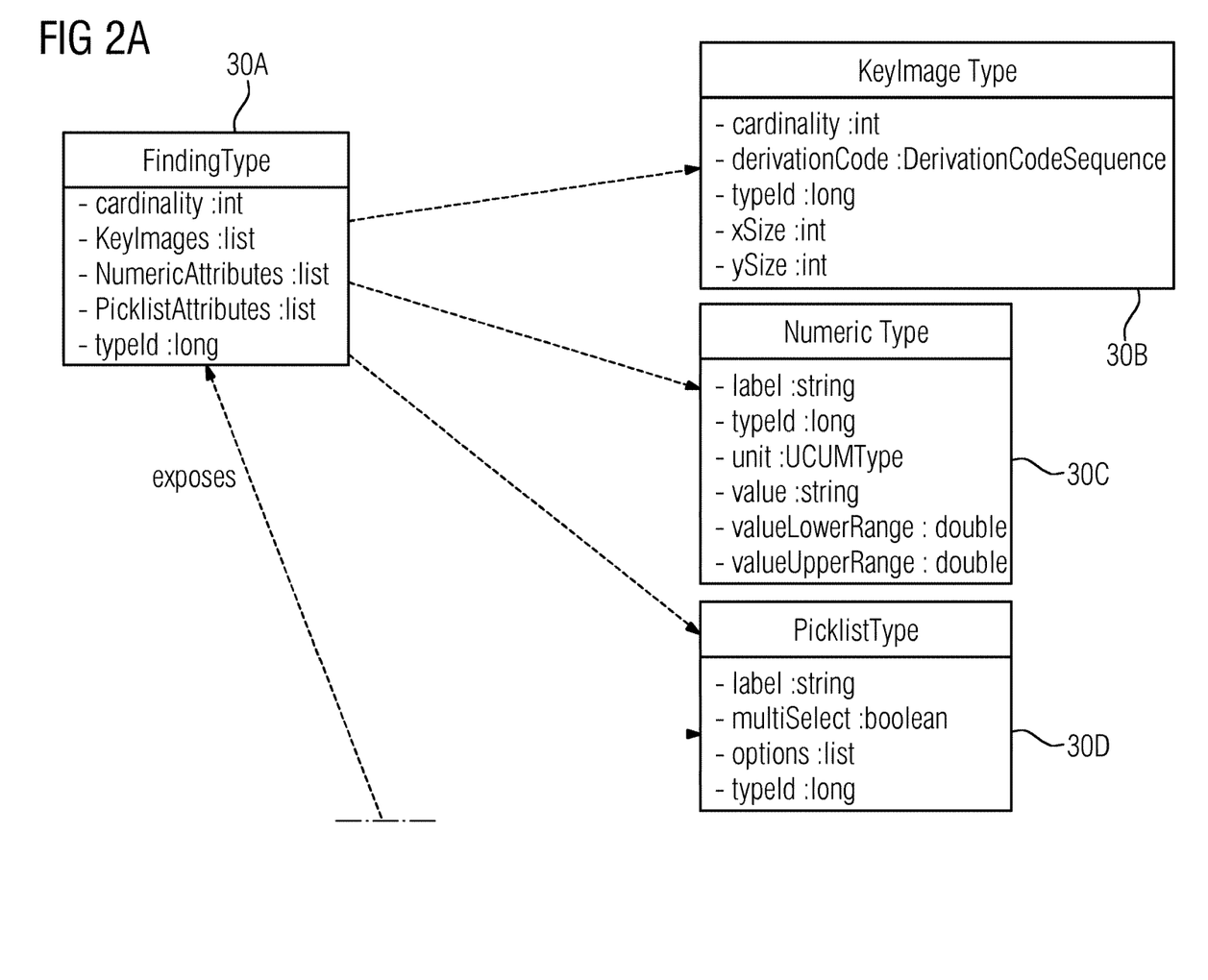
Figure 2B:
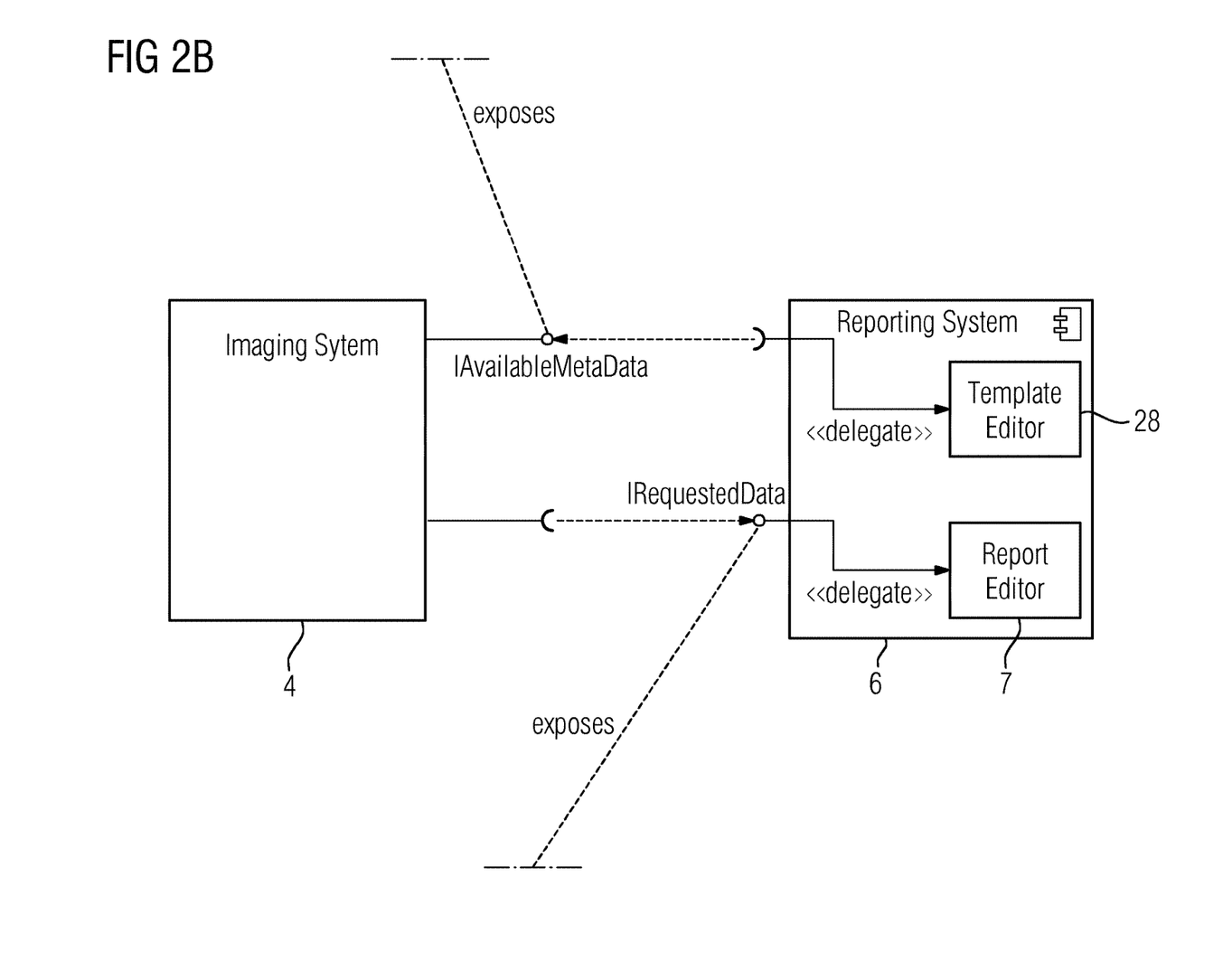
Figure 2C:
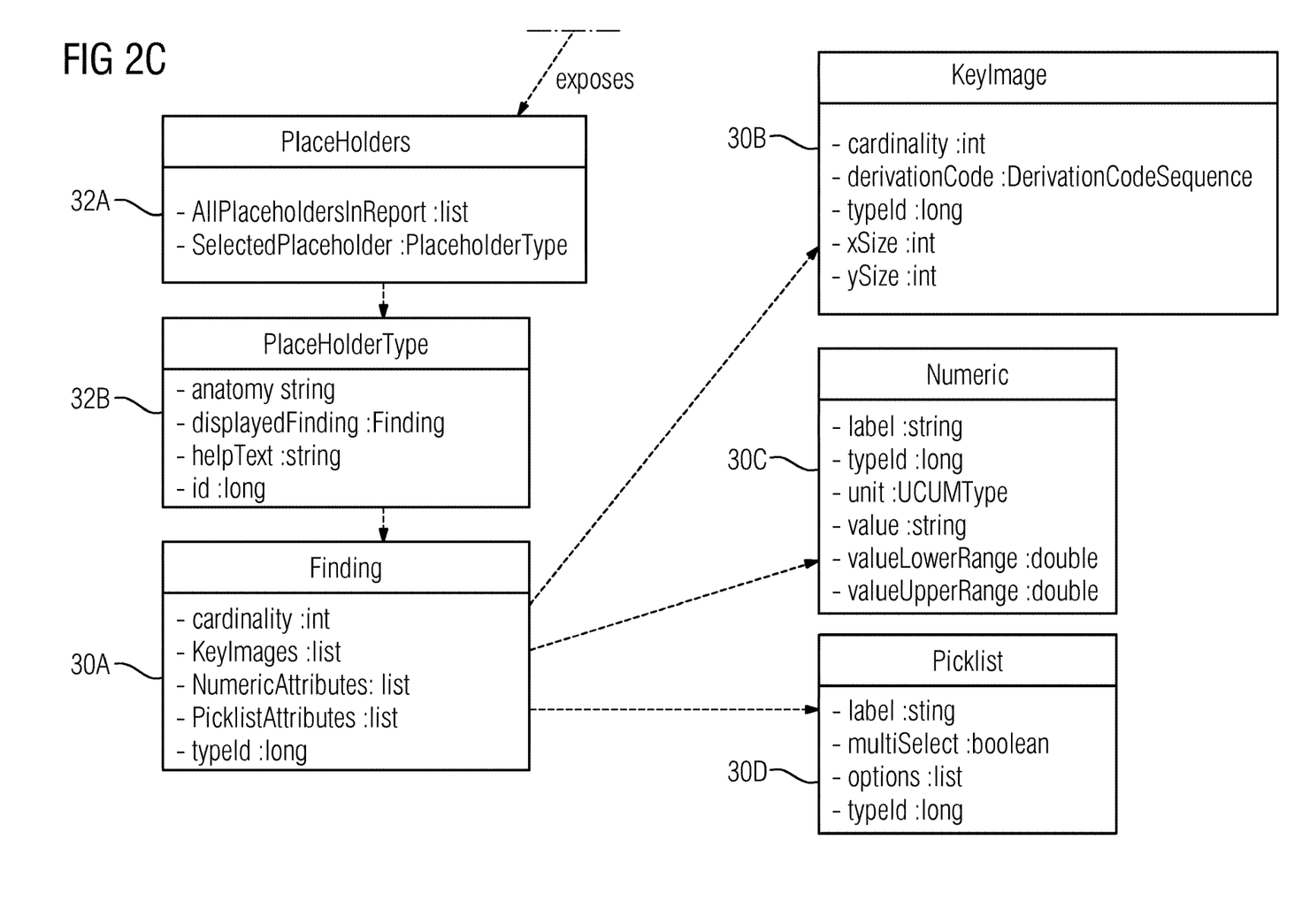

The English technical terms of UML notation used in FIG. 2 are self-explanatory in general. However, the function of the connector terms "exposes" and "delegate" are briefly explained below. "Exposes" provides that a component either provides an interface (e.g., to other components) or requires an interface (e.g., from other components). A "delegation connector" shows the connection between the external behavior of a component and internal structure or parts of the component, which realizes the behavior.

In FIG. 2B, the imaging system 4, already shown in FIG. 1, and the reporting system 6 are shown again as components in the component diagram. In addition to the report editor 11, the reporting system 4 includes a template editor 28. The template editor 28 permits the creation of report templates including placeholder fields with metadata for all the measured values, analyses and key images to be inserted in the report. The structure of the placeholder fields with the metadata provided for in the report is exemplified in FIG. 2A by the specified classes 30A to 30D with the specified attributes for the various data types.

FIG. 2C shows the structure of the data request with the placeholders and the metadata that are transferred from a particular report form to the imaging system 2 as a data request. The placeholders are organized in two classes 32A and 32B with attributes specified in FIG. 2C. The class 32B "PlaceHolderType" also includes a help text as an attribute. In addition, class 32B may contain graphic information about the analyses (e.g., about the location of the analysis). However, this is not shown here.

Figure 3:
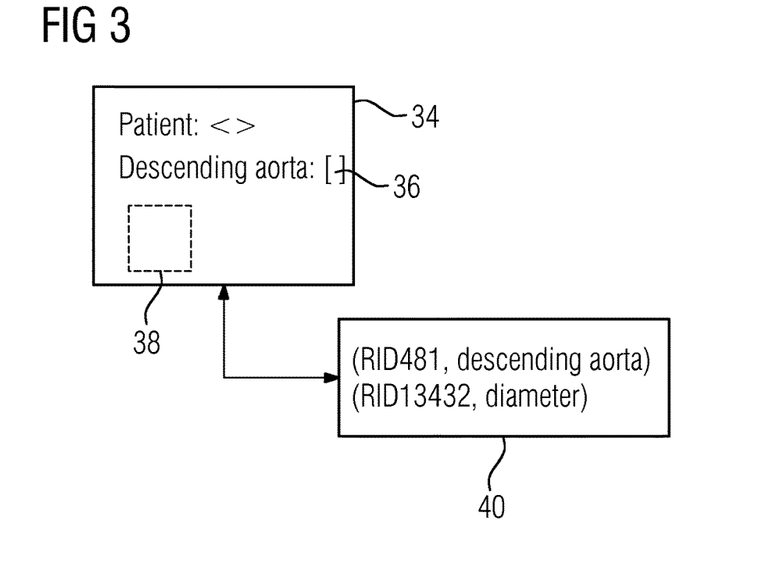
FIG. 3 shows an exemplary element from a report template with placeholders.

With reference to FIG. 3, the draft of a report form 34 (e.g., only an extract) is exemplified hereinafter for a particular data request. The creator of the report form defines a placeholder 36 of an entry field and a placeholder 38 for a key image. In addition, the metadata and attributes of the placeholder 36 are defined. In defining the placeholder 36, unique placeholder designations are selected, the meanings of which are taken from an ontology 40 such as, for example, RadLex. The placeholder 36 may contain a corresponding code as additional information.

Figure 4:
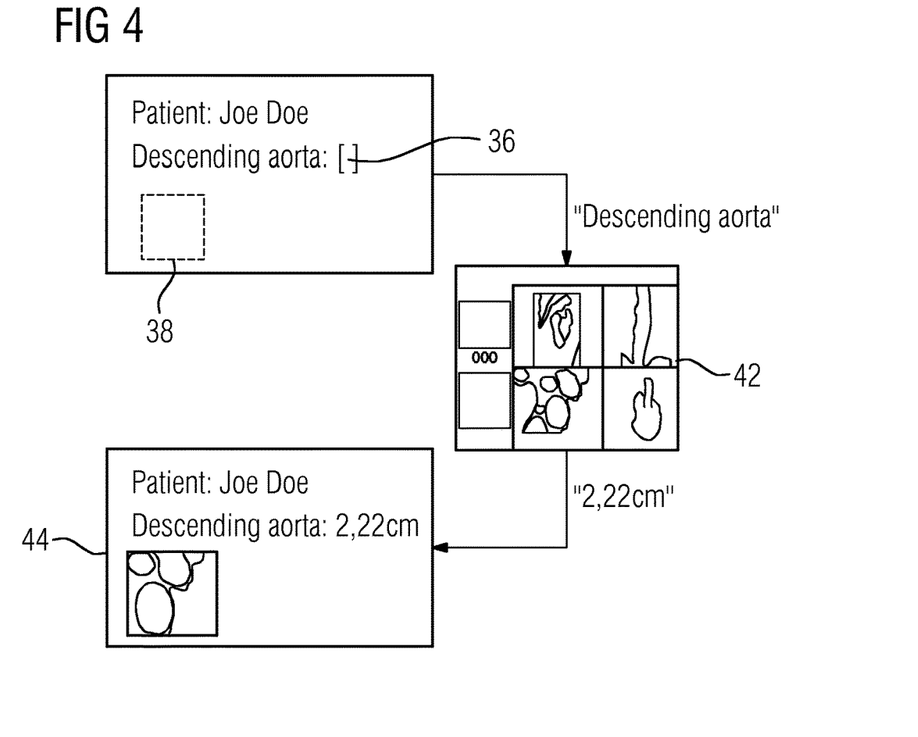
FIG. 4 shows exemplary acts for the preparation of a report.

FIG. 4 explains the procedure of measured value transmission and of the allocation of a key image in the section of the report template according to FIG. 3. After selection of the report to be used by the report editor 11, all the placeholders 36 used in the report are sent to the imaging system 4 as a data request and specified to the user 2 at the imaging system 4. This also includes, for example, the placeholder "Descending aorta" with the associated metadata "diameter" and the request for the allocation of a key image from FIG. 3. In an image display of the region for diagnosis (e.g., the descending aorta) in the imaging system 4, the user 2 quantitatively determines the diameter requested and assigns the data request "Descending aorta" to this measured value. In addition, the user 2 determines a key image supplementing the measurement. After the assignment of the requested data, this is automatically sent to the report editor 11 for completion of the report form 34. The completed section of the copy of the report is indicated in FIG. 4 by the reference character 44.

Figure 5:
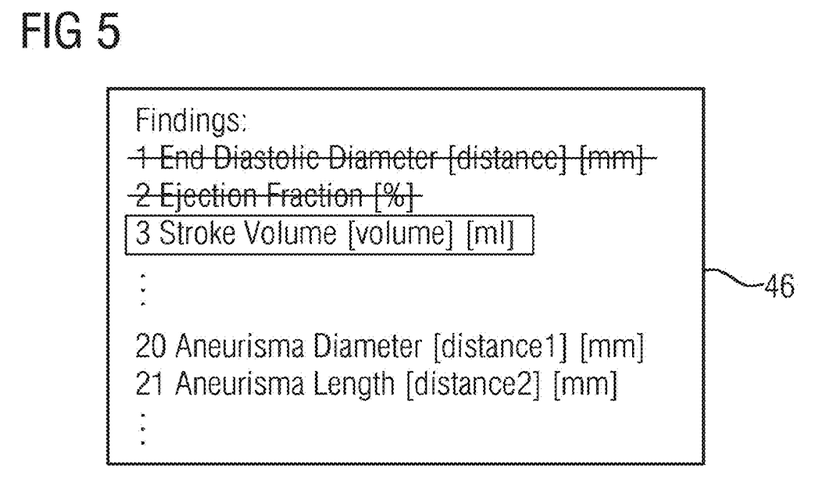
FIG. 5 shows an exemplary extract from a list of placeholder designations including the associated metadata.

FIG. 5 shows an extract from a ranked list 46 of placeholders 36 that is displayed as a data request by the imaging system 4 after loading of a report form into the imaging system 4 by the report editor 11. The list 46 contains analysis instructions for the user 2 that are processed in the specified sequence by the user 2.

The user 2 may also enter placeholder designations (e.g., the user is not limited to the placeholders provided). In this case, an auto-fill function may propose possible placeholders to the user 2.

When processing the placeholder list, the user 2 may also be assisted by the features described hereinafter. As soon as a measured value is allocated to a placeholder 36, the measured value is automatically removed from the list 46 of placeholders. Thus, for example, the two crossed-out work instructions at the start of the list show the user 2 that this requested data has already been entered in the report form. As the next measured value, the next data request, highlighted by a frame, is automatically allocated to the placeholder (e.g., "Stroke Volume") and then sent to the report editor 11. Consecutive measurement results are therefore automatically allocated to the next respective unassigned placeholder 36 in the list 46. This automatic allocation is advantageous for measurements relating to an anatomical detail such as, for example, an aneurysm.

Alternatively, a list of suggestions containing placeholders 36 of the same type that have not yet been inserted in the report to be produced may be presented to the user 2 by the imaging system 4 after the user 2 has ascertained a measured value.

Figure 6:
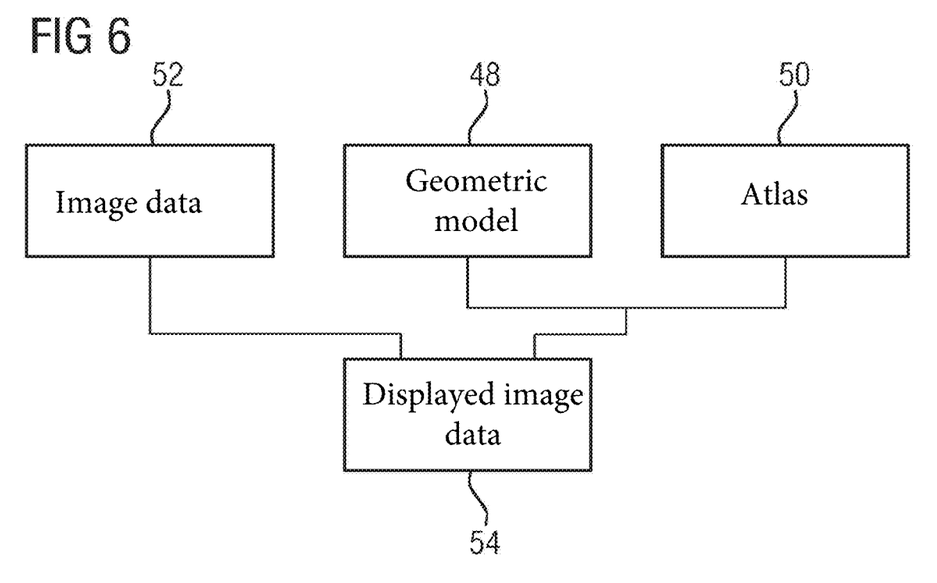
FIG. 6 shows a simplified diagram that shows an exemplary sequence of data assignment with the aid of an atlas or a model of the measurement locations.

FIG. 6 shows another additional feature supporting the user 2 for the transfer of analysis data when creating a report. In this embodiment, exclusively or in addition to the placeholder list 46, the user 2 is presented with a geometric model 48 of the allocation of the analysis locations displayed in 2D or 3D. Alternatively, an atlas 50 with analysis locations entered in the correct position may also be displayed. The model 48 or the atlas 50 are registered with the image data 52 and may be displayed optionally fused with the original image data (see reference character 54). The user 2 then performs the measurements requested for the report, where consecutive analysis data is allocated to the model 48 or the atlas 50.

The measured values may be automatically allocated to the analysis locations representing the placeholders by ascertaining the shortest Euclidean distance between a measured value and an analysis location of the measured value after the registration of image data and model or atlas. Optionally, an improvement in the robustness of the allocation of the automatic allocation may be achieved by exploiting the physical location of the individual measurements in relation to each other. The measured values snap into the associated measurement locations and are therefore allocated with implicit accuracy.

One or more of the present embodiments thus relate to the following circumstances.

For the preparation of a medical report, a user 2 interacts both with a medical imaging system 4 and with a medical reporting system 6. The medical reporting system 6 includes a collection of report templates 12 for medical reports. The report templates 12 include placeholder fields 36, 38 with unique placeholder designations and metadata 30A to 30D, 32A, 32B. After a user entry 22 in the medical imaging system 4 to select an image dataset for diagnosis, the image dataset 42 for diagnosis and analysis tools 10 are made available to the user 2. After a user entry 24 in the medical reporting system 6 to select a report template, a report template is made available. Placeholders 32A, 36, 38 contained in the selected report template are displayed with corresponding placeholder designations and metadata 32B and automatically sent to the imaging system 4 as data requests and displayed at the imaging system 4. According to the displayed data requests 32A, 46, data 30A to 30B corresponding to the data requests is ascertained or determined by the user 2 and assigned to the placeholder designations 32A, 32B. A report editor 11 automatically saves the data in the placeholder fields.

Although the invention was illustrated and described in more detail by the exemplary embodiments, the invention is not limited by the disclosed examples. Other variations can be derived therefrom by a person skilled in the art without departing from the scope of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for preparing a medical report with a medical imaging system and a medical reporting system, wherein a user interacts both with the medical imaging system and with the medical reporting system, wherein the medical imaging system and the medical reporting system are linked to each other via a data line, wherein the medical imaging system comprises a collection of analysis tools for various imaging modalities, wherein the medical reporting system comprises a collection of report templates for medical reports about various medical questions in electronic form, wherein the report templates comprise placeholder fields with unique placeholder designations and metadata, and wherein the medical reporting system comprises a report editor, the method comprising:

after a user entry in the medical imaging system to select an image dataset for diagnosis, making the image dataset for diagnosis and corresponding analysis tools of the collection of analysis tools for analysis of the image dataset for diagnosis available to the user by the medical imaging system;

after a user entry in the medical reporting system to select a report template, making the selected report template available to the medical imaging system by the medical reporting system, placeholders contained in the selected report template being displayed as data requests with placeholder designations and metadata, wherein the placeholders are automatically sent to the medical imaging system by the medical reporting system;

according to the data requests displayed, ascertaining or determining, by the user via the analysis tools of the medical imaging system, data corresponding to the data requests and assigning, by the user via the analysis tools of the medical imaging system, the data to the placeholder designations;

automatically sending the user ascertained or user designated data to the report editor by the medical imaging system together with the placeholder designations corresponding to the assigned data; and automatically saving, by the report editor, the user ascertained or user designated data in the placeholder fields of the report form corresponding to the placeholder designations.

2. The method of claim 1, wherein the placeholders and the metadata are displayed by the medical imaging system.

3. The method of claim 1, wherein the placeholder fields for measured values and image data are provided.

4. The method of claim 1, wherein the placeholders contain metadata specifying at least one data type of the data request.

5. The method of claim 1, wherein the placeholder designations are displayed in an orderly sequence for the user.

6. The method of claim 1, wherein the respective placeholder designation is no longer displayed by the medical imaging system after the user has assigned the user ascertained or user determined data to the respective placeholder designation.

7. The method of claim 1, wherein data consecutively ascertained or determined by the user is automatically assigned to consecutive placeholder designations by the medical imaging system.

8. The method of claim 1, wherein after registration of the image dataset, data, ascertained or determined using an atlas designated with corresponding placeholder designations in the area, is automatically assigned to a location with a placeholder designation in the atlas.

9. The method of claim 1, wherein the placeholder fields comprise explanatory data that is made available to the medical reporting system, the medical imaging system, or the medical reporting system and the medical imaging system for display.

10. The method of claim 9, wherein the explanatory data comprises text data.

11. The method of claim 9, wherein the explanatory data comprises graphic data.

12. The method of claim 11, wherein the graphic data contains a model representation of the data requests.

13. The method of claim 12, wherein the model representation is fused in the image dataset for diagnosis.

14. The method of claim 13, wherein consecutively ascertained or determined data is allocated to the model and automatically assigned to the placeholders.

15. An apparatus for preparing a medical report, the apparatus comprising:
   a medical imaging system; and
   a medical reporting system linked to the medical imaging system via a data line, the medical reporting system comprising a report editor and a collection of report templates for medical reports about various medical questions in electronic form, the report templates comprising placeholder fields with unique placeholder designations and metadata, wherein a user interacts both with the medical imaging system and with the medical reporting system,
   wherein after a user entry in the medical imaging system to select an image dataset for diagnosis, the medical imaging system is configured to make the image dataset for diagnosis and analysis tools for analysis of the image dataset for diagnosis available to the user,
   wherein after a user entry in the medical reporting system to select a report template, the medical reporting system is configured to make the selected report template available to the medical imaging system, placeholders contained in the selected report template being displayed as data requests with placeholder designations and metadata, wherein the placeholders are automatically sent to the medical imaging system by the medical reporting system,
   wherein according to the data requests displayed, data corresponding to the data requests is ascertainable or determinable by the user via the analysis tools of the medical imaging system, and the data is assignable to the placeholder designations by the user via the analysis tools of the medical imaging system,
   wherein the medical imaging system is configured to automatically send the user ascertained or user designated data to the report editor together with the placeholder designations corresponding to the assigned data,
   wherein the report editor is configured to automatically save the user ascertained or user designated data in the placeholder fields of the report form corresponding to the placeholder designations,
   wherein each of the medical imaging system and the medical reporting system comprises a runtime data interface, the runtime data interfaces being configured to give a data request from the medical reporting system to the medical imaging system and requested data from the medical imaging system to the medical reporting system.

16. A computer program product comprising a non-transitory computer-readable storage medium storing computer-readable computer program code having instructions that, when executed, prompts a computer or a processor to prepare a medical report with a medical imaging system and a medical reporting system, wherein a user interacts both with the medical imaging system and with the medical reporting system, wherein the medical imaging system and the medical reporting system are linked to each other via a data line, wherein the medical reporting system comprises a collection of report templates for medical reports about various medical questions in electronic form, wherein the report templates comprise placeholder fields with unique placeholder designations and metadata, and wherein the medical reporting system comprises a report editor, the instructions comprising:
   after a user entry in the medical imaging system to select an image dataset for diagnosis, making the image dataset for diagnosis and analysis tools for analysis of the image dataset for diagnosis available to the user by the medical imaging system;
   after a user entry in the medical reporting system to select a report template, making the selected report template available to the medical imaging system by the medical reporting system, placeholders contained in the selected report template being displayed as data requests with placeholder designations and metadata, wherein the placeholders are automatically sent to the medical imaging system by the medical reporting system;
   according to the data requests displayed, ascertaining or determining, by the user via the analysis tools of the medical imaging system, data corresponding to the data requests and assigning, by the user via the analysis tools of the medical imaging system, the data to the placeholder designations;
   automatically sending the user ascertained or user designated data to the report editor by the medical imaging system together with the placeholder designations corresponding to the assigned data; and
   automatically saving, by the report editor, the user ascertained or user designated data in the placeholder fields of the report form corresponding to the placeholder designations.

* * * * *